US010229498B2

United States Patent
Kitamura et al.

(10) Patent No.: US 10,229,498 B2
(45) Date of Patent: Mar. 12, 2019

(54) IMAGE PROCESSING DEVICE, IMAGE PROCESSING METHOD, AND COMPUTER-READABLE RECORDING MEDIUM

(71) Applicant: OLYMPUS CORPORATION, Tokyo (JP)

(72) Inventors: Makoto Kitamura, Hachioji (JP); Toshiya Kamiyama, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/649,700

(22) Filed: Jul. 14, 2017

(65) Prior Publication Data
US 2017/0309024 A1 Oct. 26, 2017

Related U.S. Application Data

(63) Continuation of application No. PCT/JP2015/051319, filed on Jan. 20, 2015.

(51) Int. Cl.
*G06K 9/46* (2006.01)
*G06T 7/00* (2017.01)
(Continued)

(52) U.S. Cl.
CPC ........ *G06T 7/0012* (2013.01); *A61B 1/00009* (2013.01); *A61B 1/041* (2013.01);
(Continued)

(58) Field of Classification Search
CPC ......... G06T 7/0012; G06T 2207/10081; G06T 11/006; G06T 7/0081; G06T 2207/10116;
(Continued)

(56) References Cited

U.S. PATENT DOCUMENTS 8,233,711 B2 7/2012 Wang et al.
2010/0045786 A1 2/2010 Kitamura
(Continued)

FOREIGN PATENT DOCUMENTS

JP 2008-278965 A 11/2008
JP 2010-113616 A 5/2010
(Continued)

OTHER PUBLICATIONS

International Search Report dated Apr. 14, 2015 issued in PCT/JP2015/051319.
(Continued)

*Primary Examiner* — Duy M Dang
(74) *Attorney, Agent, or Firm* — Scully, Scott, Murphy & Presser, P.C.

(57) ABSTRACT

An image processing device includes: a specific candidate area extracting unit configured to extract a specific candidate area that satisfies a predetermined condition from an intraluminal image captured inside a body lumen; a reference area setting unit configured to set a reference area that includes at least a part of the specific candidate area; a local area extracting unit configured to extract local areas based on the reference area; a local feature data calculator configured to calculate local feature data that is feature data of each of the local areas; a weight setting unit configured to set a weight depending on each of the local areas based on the specific candidate area; and a feature data integrating unit configured to integrate the local feature data.

17 Claims, 10 Drawing Sheets

(51) Int. Cl.
*A61B 1/00* (2006.01)
*G06F 19/00* (2018.01)
*G06T 7/11* (2017.01)
*A61B 1/04* (2006.01)

(52) U.S. Cl.
CPC ............ *G06F 19/30* (2013.01); *G06K 9/4676* (2013.01); *G06T 7/11* (2017.01); *G06T 2207/10024* (2013.01); *G06T 2207/10068* (2013.01); *G06T 2207/20016* (2013.01); *G06T 2207/20021* (2013.01); *G06T 2207/30032* (2013.01); *G06T 2207/30096* (2013.01)

(58) Field of Classification Search
CPC ............ G06T 2207/30004; G06T 5/40; G06T 2207/30068; G06T 7/0085; G06T 7/60; G06T 1/20; G06T 17/20; G06T 1/60; A61B 6/032; A61B 5/02007; A61B 5/7264; A61B 5/742; G06K 9/4604; G06K 9/52; G06K 9/6267; G06K 9/66; G06F 9/5044; G06F 17/5018; G06F 2217/16
See application file for complete search history.

(56) References Cited

U.S. PATENT DOCUMENTS

| | | |
|---|---|---|
| 2010/0119110 A1 | 5/2010 | Kanda |
| 2012/0051612 A1 | 3/2012 | Kitamura et al. |
| 2012/0051654 A1 | 3/2012 | Kitamura et al. |

FOREIGN PATENT DOCUMENTS

| | | |
|---|---|---|
| JP | 2012-045055 A | 3/2012 |
| JP | 2012-045057 A | 3/2012 |
| JP | 2014-030548 A | 2/2014 |
| JP | 2014-161672 A | 9/2014 |

OTHER PUBLICATIONS

Yoshimuta, Junki et al., "A System for Colorectal Endoscopic Images based on NBI Magnification Findings", IEICE Technical Report, Medical Imaging (May 12, 2011), vol. 111, No. 49, pp. 13-18, with English Abstract.

IMAGE PROCESSING DEVICE, IMAGE PROCESSING METHOD, AND COMPUTER-READABLE RECORDING MEDIUM

CROSS-REFERENCE TO RELATED APPLICATIONS

This application is a continuation of PCT international application Ser. No. PCT/JP2015/051319 filed on Jan. 20, 2015 which designates the United States, and the entire contents of the PCT international application is incorporated herein by reference.

BACKGROUND

1. Technical Field

The disclosure relates to an image processing device, an image processing method, and a computer-readable recording medium with which image processing is performed to an intraluminal image captured inside a body lumen.

2. Related Art

A method (bag of features (BoF)) has been conventionally disclosed in which local feature data are calculated from an image, and integrated feature data obtained by integrating each feature data is used to perform identification with high accuracy (for example, see U.S. Pat. No. 8,233,711 and Yasushi Yagi, Hideo Saito (ed.): Computer Vision and Image Media 3, Advanced Communication Media CO., LTD., pp. 90-95 (Nov. 25, 2010)). Processing procedures of the method are as follows.

Procedure 1. Local feature data are calculated from within an image.

Procedure 2. The image is divided into rectangular areas having a plurality of sizes to generate a pyramid image.

Procedure 3. Distance in a local feature space between local feature data in each rectangular area and a group of representative vectors generated in advance is calculated, a nearest representative vector is obtained, and a frequency distribution (integrated feature data) thereof is calculated.

Procedure 4. The frequency distribution calculated for each rectangular area and a frequency distribution of normality and abnormality generated in advance are compared to determine normality/abnormality.

SUMMARY

In some embodiments, an image processing device includes: a specific candidate area extracting unit configured to extract a specific candidate area that satisfies a predetermined condition from an intraluminal image captured inside a body lumen; a reference area setting unit configured to set a reference area that includes at least a part of the specific candidate area; a local area extracting unit configured to extract local areas based on the reference area; a local feature data calculator configured to calculate local feature data that is feature data of each of the local areas; a weight setting unit configured to set a weight depending on each of the local areas based on the specific candidate area; and a feature data integrating unit configured to integrate the local feature data.

In some embodiments, an image processing method includes: extracting a specific candidate area that satisfies a predetermined condition from an intraluminal image captured inside a body lumen; setting a reference area that includes at least a part of the specific candidate area; extracting local areas based on the reference area; calculating local feature data that is feature data of each of the local areas; setting a weight depending on each of the local areas based on the specific candidate area; and integrating the local feature data.

In some embodiments, a non-transitory computer-readable recording medium recording an image processing program is provided. The program causes a computer to execute: extracting a specific candidate area that satisfies a predetermined condition from an intraluminal image captured inside a body lumen; setting a reference area that includes at least a part of the specific candidate area; extracting local areas based on the reference area; calculating local feature data that is feature data of each of the local areas; setting a weight depending on each of the local areas based on the specific candidate area; and integrating the local feature data.

The above and other features, advantages and technical and industrial significance of this disclosure will be better understood by reading the following detailed description of presently preferred embodiments of the disclosure, when considered in connection with the accompanying drawings.

DETAILED DESCRIPTION

Hereinbelow, modes for carrying out the present invention (hereinafter referred to as "embodiments") will be described.

First Embodiment

Figure 1:
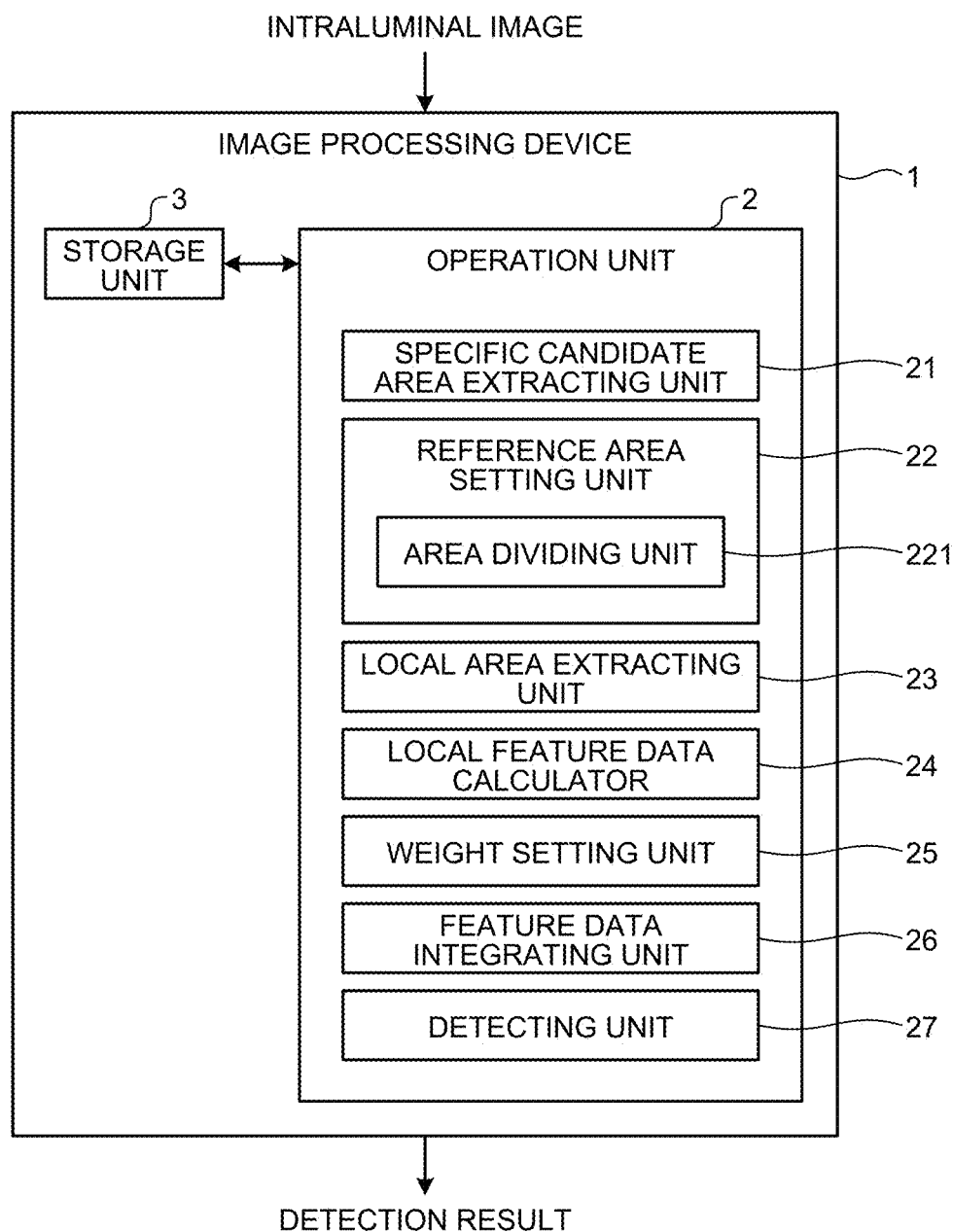
FIG. 1 is a block diagram illustrating a functional configuration of an image processing device according to a first embodiment of the disclosure.

FIG. 1 is a block diagram illustrating a functional configuration of an image processing device according to a first embodiment of the disclosure. The image processing device 1 illustrated in the figure includes an operation unit 2 and a storage unit 3. The image processing device 1 has a function to detect a specific area which satisfies a predetermined condition in an intraluminal image captured by a capsule endoscope. As the intraluminal image, a color image is used which has a pixel level (pixel value) with respect to red (R), green (G), and blue (B) wavelength components in each pixel position.

The operation unit 2 includes a specific candidate area extracting unit 21, a reference area setting unit 22, a local area extracting unit 23, a local feature data calculator 24, a weight setting unit 25, a feature data integrating unit 26, and a detecting unit 27. The specific candidate area extracting unit 21 extracts a specific candidate area corresponding to an abnormal site such as a lesion in an intraluminal image. The reference area setting unit 22 sets a reference area including the specific candidate area. The local area extracting unit 23 extracts local areas from the reference area. The local feature data calculator 24 calculates local feature data, which is feature data of each of the extracted local areas. The weight setting unit 25 sets a weight for each local feature data based on the specific candidate area. The feature data integrating unit 26 integrates the local feature data based on the set weights. The detecting unit 27 detects a specific area based on the integrated local feature data.

The specific candidate area extracting unit 21 extracts a specific candidate area corresponding to an abnormal site such as a lesion from an intraluminal image based on color feature data and/or shape feature data. For example, an aphtha, an ulcer, and the like present a specific color of white, and bleeding and redness present a specific color of red. A polyp and a tumor are often presented as a circular area. The specific candidate area extracting unit 21 extracts a specific candidate area, which is a possible candidate for such a specific area, based on the color feature data and/or the shape feature data.

First, a case will be described in which the specific candidate area extracting unit 21 extracts a specific candidate area based on the color feature data. In that case, the specific candidate area extracting unit 21 extracts, for example, a specific color area having color feature data of white color and red color as the specific candidate area. Specifically, the specific candidate area extracting unit 21 determines determination standards (color range) of a specific area based on color feature data and causes the storage unit 3 to store the determination standards. The color feature data includes pixel values of each of R, G, and B components in the specific area collected in advance, values secondarily calculated through known conversion based on the pixel values, a color difference (YCbCr conversion), a hue, saturation (HSI conversion), and a color ratio (G/R, B/G). Then, the specific candidate area extracting unit 21 determines whether each pixel is a specific candidate area based on the color feature data in each pixel to be processed and the determination standards.

Although the method has been described here in which the specific candidate area is extracted based on the determination standards generated in advance, any method may be adopted as long as it is a method with which the specific color area can be extracted from within the image. For example, the specific candidate area may be extracted by a method based on a feature space distance from a representative color feature data. Alternatively, instead of using color feature data on a per pixel basis, an image may be divided into small areas based on edge information in the image and then color feature data on a per small area basis may be used.

Next, a case will be described in which the specific candidate area extracting unit 21 extracts a specific candidate area based on the shape feature data. In that case, the specific candidate area extracting unit 21 extracts, for example, an area having shape feature data corresponding to a circular shape as the specific candidate area. Specifically, gradient strength of each pixel (such as a luminance value and a G value) in an image is calculated by known Sobel, Laplacian, or the like. A correlation value between the calculated gradient strength and a circular model generated in advance is calculated, and a circular area of which the correlation value is greater than or equal to a predetermined threshold is extracted as the specific candidate area.

Although the method has been described here in which the specific candidate area is extracted by performing pattern matching with the circular model generated in advance, any method may be adopted as long as it is a method with which the circular area can be extracted from within the image. For example, known methods such as Hough transform, random sample consensus (RANSAC), deformable part model (DPM), and ellipse and line segment detector (ELSD) may be adopted.

The reference area setting unit 22 sets a reference area by extracting a circumscribed rectangular area where the specific candidate area is circumscribed, and deforming the circumscribed rectangular area. The reference area setting unit 22 includes an area dividing unit 221 which divides the reference area into at least a border area and an internal area. The area dividing unit 221 reduces the circumscribed rectangular area where the specific candidate area is circumscribed to extract a reduced area, and performs division setting such that the reference area is divided into the border area and the internal area based on the reduced area.

The local area extracting unit 23 extracts a representative pixel position from the reference area, and extracts, as a local area, a predetermined area centered at the pixel position. The local area extracting unit 23 may extract the pixel positions at regular intervals, or at random. Alternatively, the local area extracting unit 23 extracts, as the local area, a area having a circular shape with a predetermined radius centered at the pixel position.

The local feature data calculator 24 calculates, as local feature data, any of color feature data (such as an average value of RGB, an average value of YCbCr, an average value of HSI, an average value of G/R, and an average value of B/G), texture feature data (such as local binary pattern (LBP), variance, skewness, and kurtosis), and gradient feature data (such as histograms of oriented gradients (HoG), and scale-invariant feature transform (SIFT)), in each local area, for example. The feature data described above are by way of example only, and other feature data can be used.

The weight setting unit 25 sets a weight for local feature data based on a result of the division setting of the reference area. Information in the vicinity of a border of the specific area serves as important information when detecting the specific area. Therefore, the weight setting unit 25 sets a high integration ratio for the local feature data present in the vicinity of the border when integrating the local feature data.

The feature data integrating unit 26 integrates the local feature data using, for example, the above-described known BoF based on the weights set with respect to the local feature data.

The detecting unit 27 detects the specific area based on the integrated local feature data, for example, by a known classifier such as a support vector machine (SVM) (regarding the SVM, for example, see Computer Vision and Image Media 3, Advanced Communication Media CO., LTD., pp. 95-102).

The operation unit 2 is configured by using hardware such as a central processing unit (CPU) or various operation circuits, performs instructions and data transmission to each unit constituting the image processing device 1 by reading various programs stored in the storage unit 3, and integrally controls operations of the image processing device 1 as a whole.

The storage unit 3 stores information regarding a weight coefficient set by the weight setting unit 25. The storage unit 3 is realized by various IC memories such as a read only memory (ROM) or a random access memory (RAM), a built-in hard disk or a hard disk connected by a data communication terminal, an information storage device such as a CD-ROM and a reader thereof, or the like. The storage unit 3 stores, in addition to image data of intraluminal images acquired by the image processing device 1, a program to cause the image processing device 1 to operate and to cause the image processing device 1 to execute various functions, data used during the execution of the program, and the like. Specifically, the storage unit 3 stores an image processing program according to the present embodiment, and various parameters such as a threshold used in the image process.

Various programs such as the image processing program stored by the storage unit 3 can be stored also in a computer-readable storage medium. In addition, storage of the various programs in the storage unit 3 or a storage medium may be performed when a computer or the storage medium is shipped as a product, or may be performed through download via a communication network. The communication network described herein is one realized, for example, by an existing public network, a local area network (LAN) or a wide area network (WAN), regardless of whether it is wired or wireless.

The image processing device 1 having the above configuration may be realized by using one computer, or by using a plurality of computers. In the latter case, it is also possible for the computers to perform a process in cooperation with each other while transmitting and receiving data via the communication network. The computer described herein can be configured by a general-purpose personal computer, a server, or the like.

Figure 2:
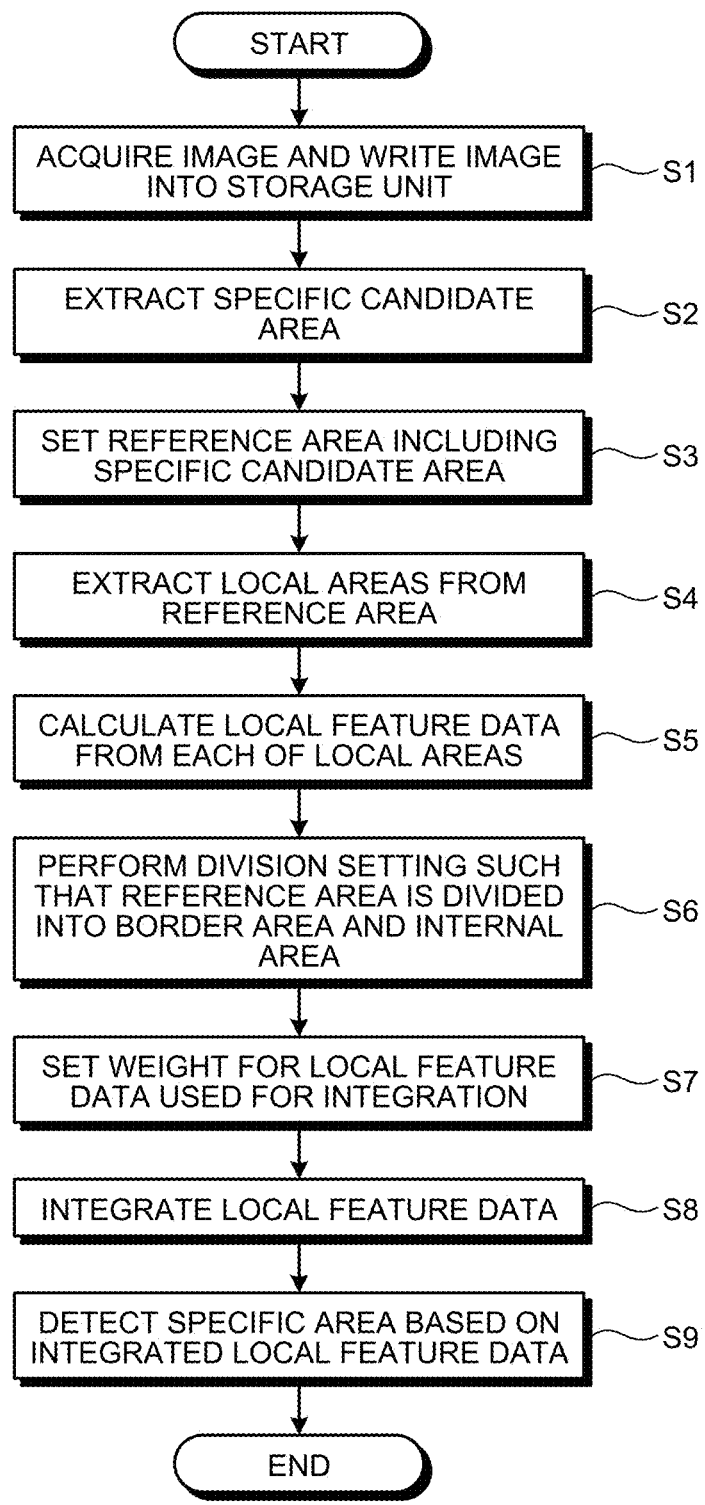
FIG. 2 is a flowchart illustrating an outline of a process executed by the image processing device according to the first embodiment of the disclosure.

FIG. 2 is a flowchart illustrating an outline of a process executed by the image processing device 1. First, in Step S1, the operation unit 2 acquires an intraluminal image to be processed, and writes the image into the storage unit 3 (Step S1).

In Step S2, the specific candidate area extracting unit 21 extracts a specific candidate area from within the intraluminal image based on color feature data and/or shape feature data (Step S2). By Step S2, the specific candidate area corresponding, for example, to an aphtha, an ulcer, a polyp or a tumor is extracted.

Figure 3:
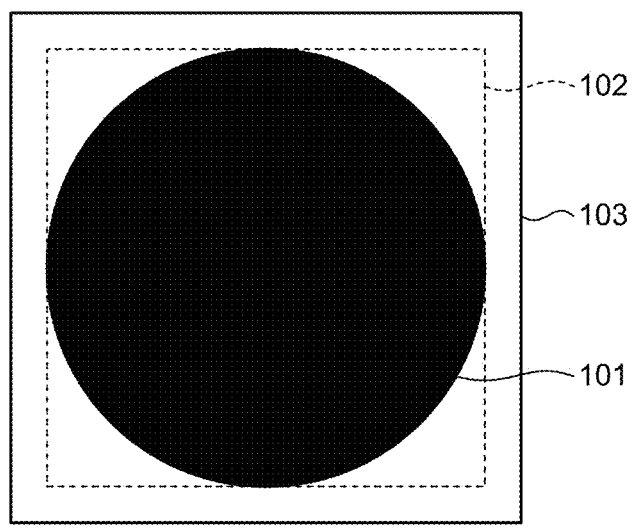
FIG. 3 is a diagram schematically illustrating a reference area setting process performed by a reference area setting unit included in the image processing device according to the first embodiment of the disclosure.

In Step S3, the reference area setting unit 22 sets a reference area including the specific candidate area (Step S3). FIG. 3 is a diagram schematically illustrating a reference area setting process performed by the reference area setting unit 22. Hereinbelow, an outline of the reference area setting process will be described with reference to FIG. 3.

First, the reference area setting unit 22 performs a labeling process to the specific candidate area. As the labeling process, for example, a known labeling process described in Digital Image Processing, Computer Graphic Arts Society, pp. 181-182, can be applied.

Subsequently, the reference area setting unit 22 extracts a circumscribed rectangular area 102 of the specific candidate area 101.

Then, the reference area setting unit 22 sets, as the reference area 103, an expanded area obtained by expanding the circumscribed rectangular area 102 by a factor of n (1.0<n≥2.0). At that time, the n value is defined, for example, based on an area of the specific candidate area 101, as n=1.0+(area of the specific candidate area/maximum area) . . . (1). Here, the maximum area is a reference area for setting a circumscribed rectangular area, and corresponds to a maximum value of an area assumed as a specific candidate area.

In Step S4, the local area extracting unit 23 extracts local areas from the reference area (Step S4).

First, the local area extracting unit 23 extracts, from within the reference area 103, pixel positions at regular intervals (or at random).

Figure 4:
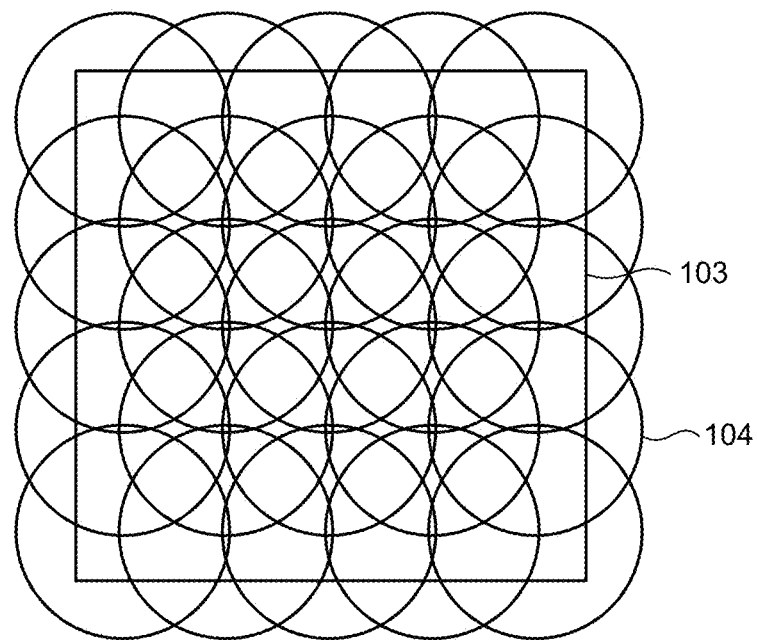
FIG. 4 is a diagram schematically illustrating a local area extraction process performed by a local area extracting unit included in the image processing device according to the first embodiment of the disclosure.

Subsequently, as illustrated in FIG. 4, the local area extracting unit 23 extracts circular areas centered at the extracted pixel positions, respectively, as a local area 104. Although the method (called DENS) has been described here in which the local area extracting unit 23 extracts circular areas from within the reference area at regular intervals, the local areas may be extracted from within the reference area by using known SIFT (key point detection) in addition to the above method (for example, see Computer Vision and Image Media 2, Advanced Communication Media CO., LTD., pp. 5-22).

In Step S5, the local feature data calculator 24 calculates local feature data from each of the local areas (Step S5).

In Step S6, the area dividing unit 221 performs division setting such that the reference area is divided into a border area and an internal area (Step S6).

Figure 5:
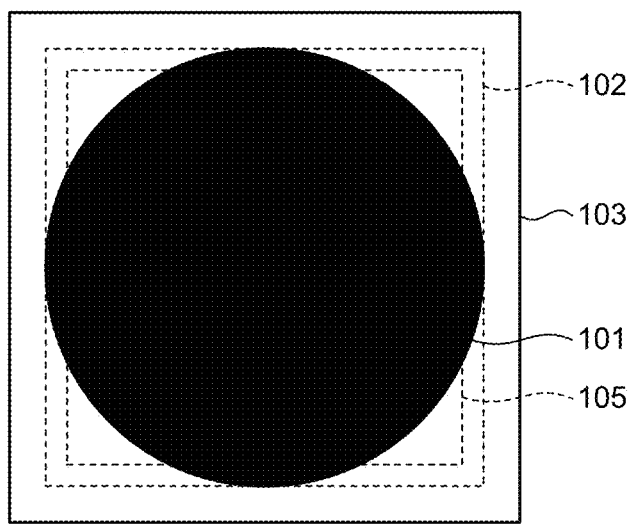
FIG. 5 is a diagram schematically illustrating a reduced area extraction process performed by an area dividing unit included in the image processing device according to the first embodiment of the disclosure.

First, the area dividing unit 221 extracts a reduced area 105 obtained by multiplying the circumscribed rectangular area 102 by a factor of n (0.5≤n<1.0), as illustrated in FIG. 5. At that time, the n value is defined, for example, based on the area of the specific candidate area 101, as n=1.0−(area of the specific candidate area/maximum area)×0.5 . . . (2).

Figure 6:
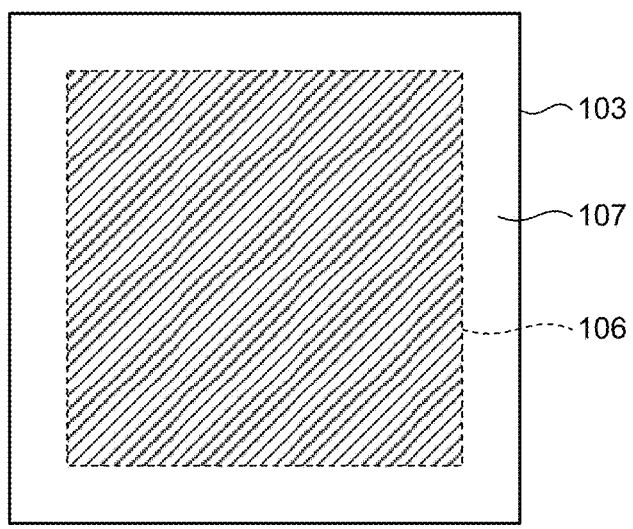
FIG. 6 is a diagram schematically illustrating a division setting process performed by the area dividing unit included in the image processing device according to the first embodiment of the disclosure.

Subsequently, the area dividing unit 221 performs division setting such that the reduced area 105 is set as an internal area 106 and the reference area 103 which is not included in the reduced area 105 is set as a border area 107, as illustrated in FIG. 6.

In Step S7, the weight setting unit 25 sets a weight for local feature data based on a result of the division setting of the reference area (Step S7). As describe above, the weight setting unit 25 sets a high integration ratio for the local feature data present in the vicinity of the border when integrating the local feature data. Specifically, the weight setting unit 25 reads predetermined weight coefficients k1 (=a weight coefficient of the border area), k2 (=a weight coefficient of the internal area), and k3 (=a weight coefficient of a remaining area other than the border area and the internal area) from the storage unit 3. Here, the weight coefficients k1 to k3 satisfy k1>k2>k3 and k1+k2+k3=1.0. The remaining area is defined as an area of a predetermined range outside the reference area, and defined as an area having about two to three times as large area as the reference area, for example.

In Step S8, the feature data integrating unit 26 integrates the local feature data using the weight coefficients k1 to k3 (Step S8). Specifically, when calculating a frequency distribution of a nearest representative vector in the BoF described above, the feature data integrating unit 26 multiplies frequencies of the representative vectors in the border area, the internal area, and the remaining area by the weight coefficients k1 to k3, respectively. Here, the representative vector is a vector defined according to a cluster when performing clustering of local feature data in a feature data space, and is a vector defined according to a centroid of the cluster, for example.

Figure 7:
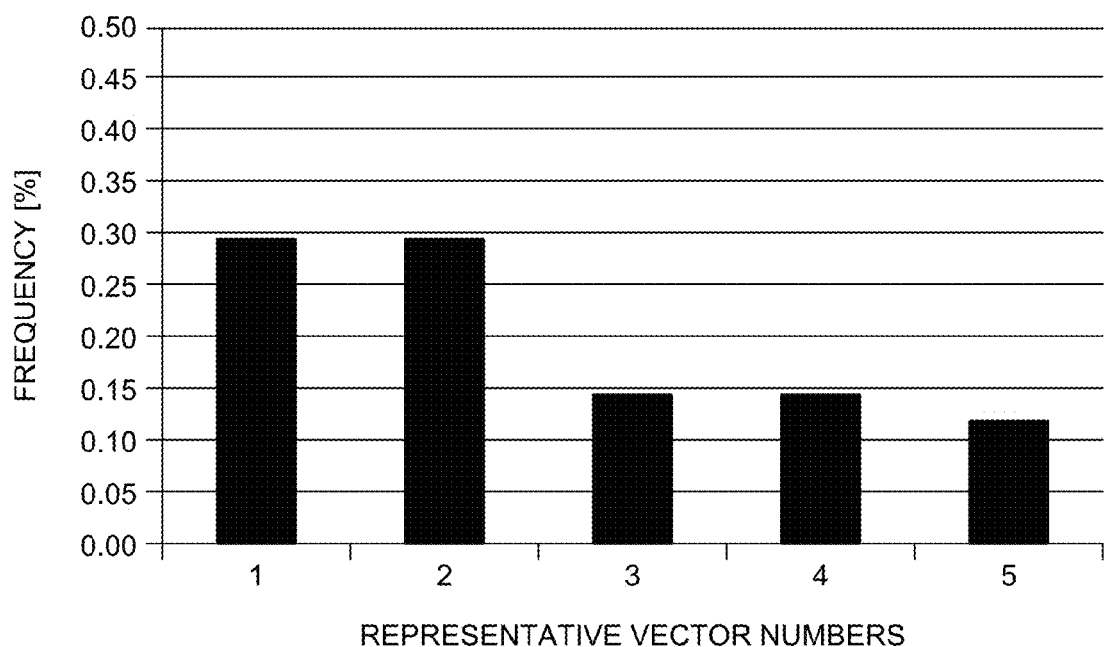
FIG. 7 is a diagram illustrating an example of a frequency distribution of representative vectors calculated by the image processing device according to the first embodiment of the disclosure.
Figure 8:
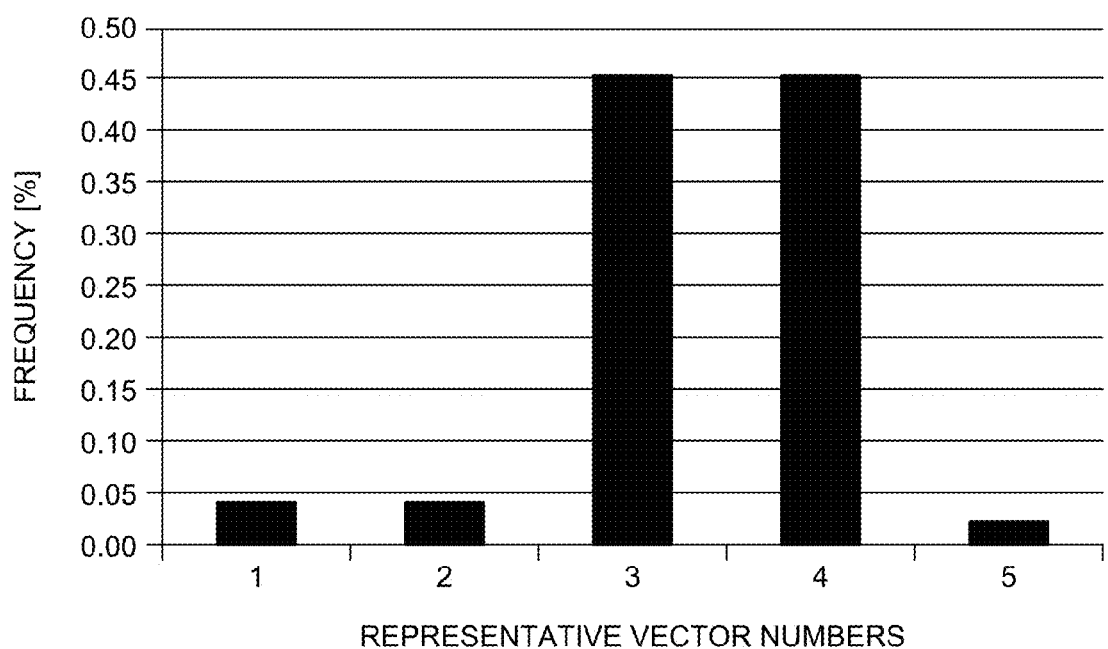
FIG. 8 is a diagram illustrating an example of a frequency distribution of the representative vectors obtained when the same representative vectors as those in FIG. 7 are not multiplied by corresponding weight coefficients, respectively.

FIG. 7 is a diagram illustrating an example of a frequency distribution of the representative vectors obtained in Step S8. FIG. 8 is a diagram illustrating an example of a frequency distribution of the representative vectors obtained when the same representative vectors as those in FIG. 7 are not multiplied by corresponding weight coefficients, respectively. When FIG. 7 and FIG. 8 are compared with each other, it can be seen that the representative vectors Nos. 1 and 2 have the largest weight coefficient, and the representative vectors Nos. 3 and 4 have the smallest weight coefficient. In other words, it can be seen that the representative vectors Nos. 1 and 2 correspond to the local feature data in the border area (weight coefficient k1), and the representative vector No. 5 corresponds to the local feature data in the internal area (weight coefficient k2), and the representative vectors Nos. 3 and 4 correspond to the local feature data in the remaining area (weight coefficient k3). As described above, in the first embodiment, the specific area can be extracted with high accuracy by integrating local feature data in which information of the border area is relatively increased by multiplying weight coefficients.

In Step S9, the detecting unit 27 detects the specific area based on the integrated local feature data (Step S9). Specifically, the detecting unit 27 detects the specific area by a known classifier such as the SVM as described above.

According to the first embodiment of the disclosure described above, since a weight is set for local feature data in each local area in an intraluminal image and the local feature data is integrated based on the weight, it is possible to calculate local feature data with which an object can be identified with high accuracy.

According to the first embodiment, by setting a weight used when integrating the local feature data based on information of the specific candidate area, the local feature data required for expressing an object is sufficiently included in a set of the integrated local feature data.

According to the first embodiment, by performing division setting such that the reference area is divided into the border area and the internal area to set a weight for each area, the local feature data can be calculated with higher accuracy. In particular, by relatively increasing the weight for the border area, more information of the border area can be acquired and higher accuracy of the local feature data can be realized.

In the first embodiment, after the reference area setting unit 22 sets the reference area, the area dividing unit 221 may perform division setting such that the reference area is divided into the border area and the internal area, and the weight setting unit 25 may set extraction density (the number of extracts of the local feature data per unit area) of the local areas such that the extraction density is decreased in the order of the border area, the internal area, and the remaining area. In that case, the local area extracting unit 23 extracts local areas at random for each area subjected to the division setting in accordance with the set extraction density. Then, the local feature data calculator 24 calculates the local feature data, and the feature data integrating unit 26 integrates the local feature data. In a case where the extraction density of each of the local areas is restricted in accordance with the divided areas as described above, speeding up of the process is realized.

Variation 1-1

Another example (second example) of the area division performed by the area dividing unit 221 will be described. In the present variation 1-1, the area dividing unit 221 calculates color information (color feature data) from the intraluminal image, and performs division setting based on the calculated color information.

First, the area dividing unit 221 calculates color feature data (such as an average value of RGB, an average value of YCbCr, an average value of HSI, an average value of G/R, and an average value of B/G) in each pixel in the reference area.

Subsequently, the area dividing unit 221 calculates an average value of color feature data in the specific candidate area.

Then, the area dividing unit 221 performs integration of similar areas by a known area integration method (for example, see Digital Image Processing, Computer Graphic Arts Society, p. 198) with respect to areas having color feature data similar to the specific candidate area.

Finally, the area dividing unit 221 performs division setting such that the integrated area is set as an internal area and the reference area which is not included in the integrated area is set as a border area.

Variation 1-2

Another example (third example) of the area division performed by the area dividing unit 221 will be described. In the present variation 1-2, the area dividing unit 221 performs shape fitting with respect to the intraluminal image, and performs division setting based on a result of the fitting.

First, the area dividing unit 221 calculates gradient strength of each pixel (such as a luminance value and a G value) in the reference area by a known filter such as Sobel, Laplacian, or the like.

Subsequently, the area dividing unit 221 calculates a correlation value between the calculated gradient strength and a specific shape model generated in advance, and extracts a specific shape area which has the largest correlation value. As the specific shape, for example, a circular shape may be applied.

Then, the area dividing unit 221 performs division setting such that the extracted circular area is set as an internal area and the reference area which is not included in the internal area is set as a border area.

Variation 1-3

Another example (fourth example) of the area division performed by the area dividing unit 221 will be described. In the present variation 1-3, the area dividing unit 221 calculates profile information of pixel values from the intraluminal image, and performs division setting based on the profile information.

Figure 9:
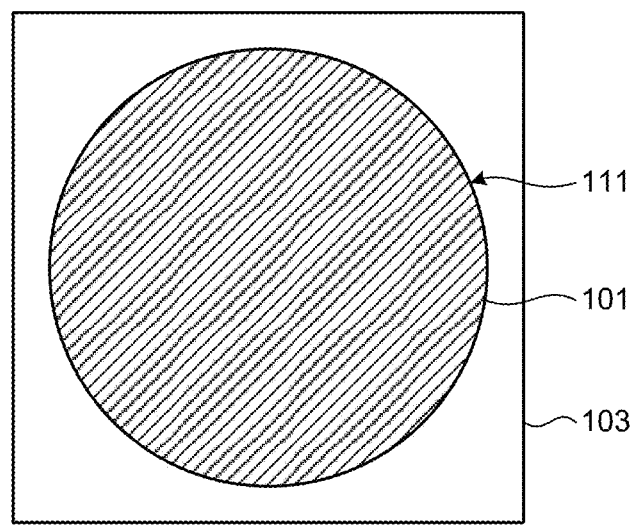
FIG. 9 is a diagram schematically illustrating a distance image calculation process performed by an area dividing unit included in an image processing device according to a variation 1-3 of the first embodiment of the disclosure.

First, as illustrated in FIG. 9, the area dividing unit 221 sets, as a border pixel 111, a pixel of interest which is a specific candidate area and any of adjacent pixels (eight neighboring pixels) of which is not a specific candidate area, for each reference area.

Figure 10:
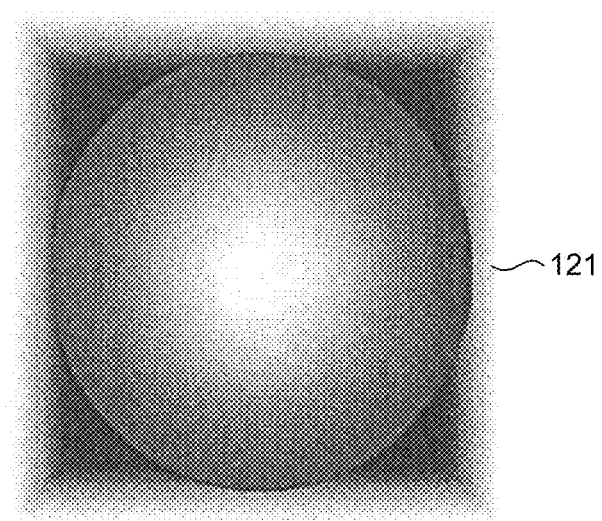
FIG. 10 is a view schematically illustrating a distance image calculated by the area dividing unit included in the image processing device according to the variation 1-3 of the first embodiment of the disclosure.

Subsequently, the area dividing unit 221 calculates a distance image from the border pixel, as illustrated in FIG. 10. At that time, the area dividing unit 221 applies a ± sign to a distance value according to whether it resides inside or outside the specific candidate area. In a case of a distance image 121 illustrated in FIG. 10, the longer the distance from the border pixel, the whiter the color, and the shorter the distance from the border pixel, the blacker the color.

Then, the area dividing unit 221 calculates an average value of pixels (such as an RGB value) which are the same distance from the border pixel.

Subsequently, the area dividing unit 221 calculates differences between average values of pixels present in an adjacent (neighbor) distance, and calculates distance at which the difference between pixel values is maximum.

Finally, the area dividing unit 221 performs division setting such that an area outside a position at which the difference between pixel values is maximum is set as a border area, and an area inside the position is set as an internal area in the reference area.

It goes without saying that the above-described variations 1-1 to 1-3 have similar effects as the first embodiment.

Second Embodiment

Figure 11:
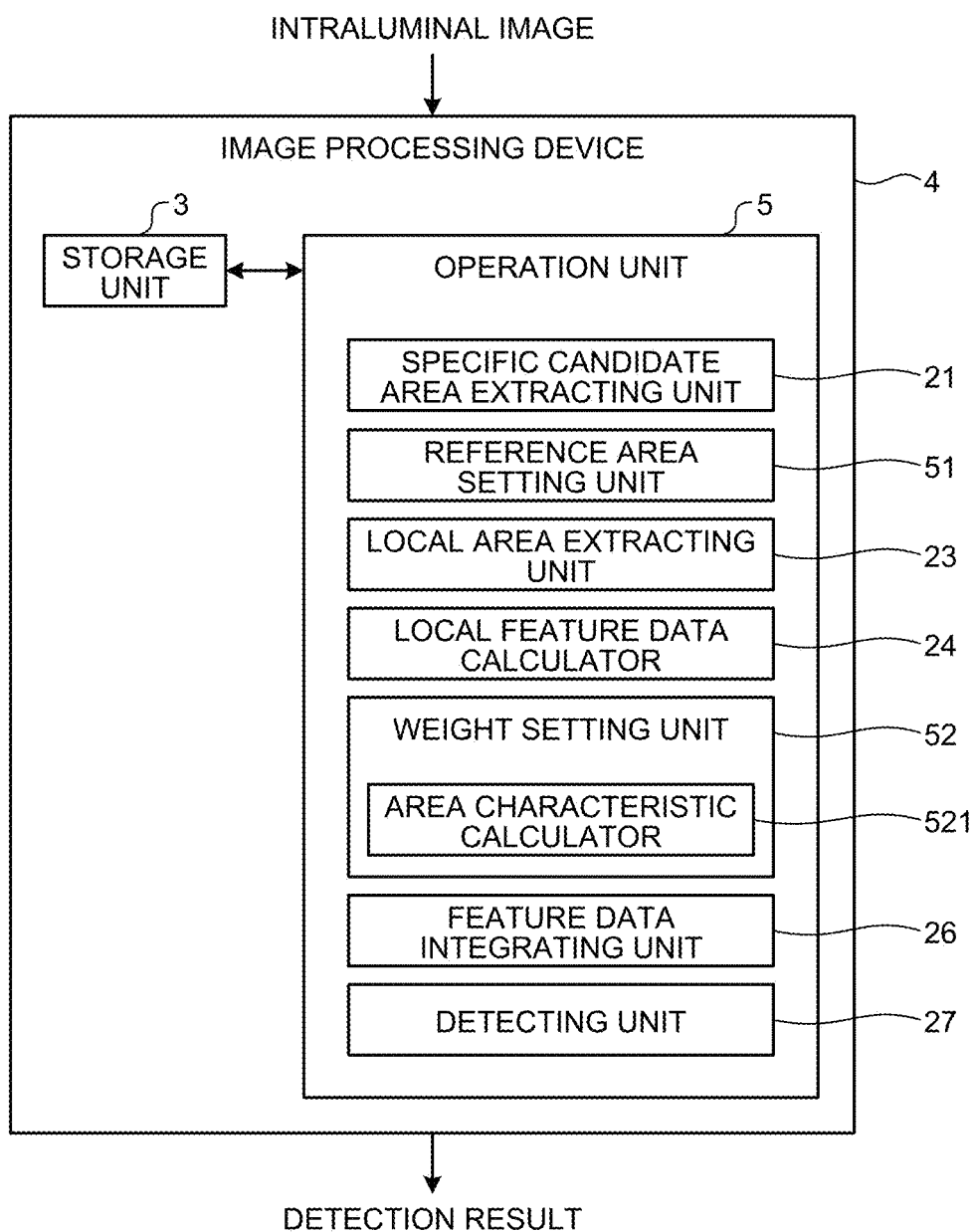
FIG. 11 is a block diagram illustrating a functional configuration of an image processing device according to a second embodiment of the disclosure.

FIG. 11 is a block diagram illustrating a functional configuration of an image processing device according to a second embodiment of the disclosure. The image processing device 4 illustrated in the figure includes an operation unit 5 and a storage unit 3. In the following description, the same reference signs are attached to components similar to those included in the operation unit 2 of the image processing device 1 according to the first embodiment.

The operation unit 5 includes a specific candidate area extracting unit 21, a reference area setting unit 51, a local area extracting unit 23, a local feature data calculator 24, a weight setting unit 52, a feature data integrating unit 26, and a detecting unit 27.

Unlike the reference area setting unit 22 described in the first embodiment, the reference area setting unit 51 does not include the area dividing unit 221. Except for the above point, the reference area setting unit 51 has similar functions as the reference area setting unit 22.

The weight setting unit 52 includes an area characteristic calculator 521 which calculates a characteristic of a local area by extracting a mucosal area present at a three-dimensional depth position similar to a specific candidate area based on a depth distance to the position.

Figure 12:
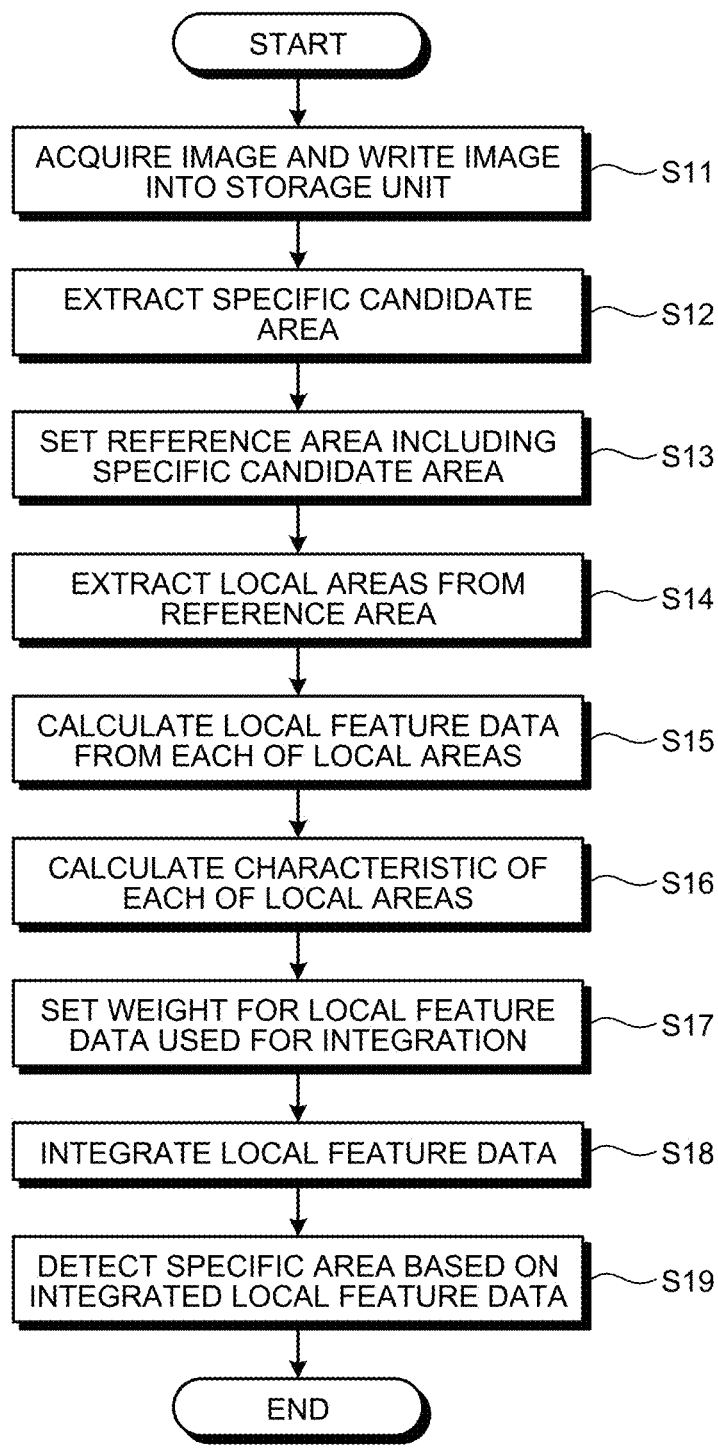
FIG. 12 is a flowchart illustrating an outline of a process performed by the image processing device according to the second embodiment of the disclosure.

FIG. 12 is a flowchart illustrating an outline of a process performed by the image processing device 4. Processes in Steps S11 to S15 are similar to those in Steps S1 to S5 in FIG. 2, respectively.

In Step S16, the area characteristic calculator 521 calculates a characteristic of a local area (Step S16). Hereinbelow, a process of the area characteristic calculator 521 will be described in detail.

First, the area characteristic calculator 521 calculates a value of an R component, which is a wavelength component hard to absorb and scatter in a living body, as a three-dimensional depth distance. The depth distance in an image may be calculated by other methods.

Subsequently, the area characteristic calculator 521 calculates an average distance of a specific candidate area.

Then, the area characteristic calculator 521 calculates an absolute value of difference between the average distance of the specific candidate area and an average distance of a corresponding local area.

Finally, the area characteristic calculator 521 determines that, regarding a local area which has an absolute value of difference smaller than or equal to a predetermined value, the local area is present at a similar depth position.

In Step S17, the weight setting unit 52 sets a weight for local feature data based on the characteristic of the local feature data (Step S17). The weight setting unit 52 sets a large integration ratio for the local feature data present at the depth position similar to the corresponding specific candidate area. Specifically, the weight setting unit 52 reads predetermined weight coefficients k11 (=a weight for local feature data present at the similar depth position), and k12 (=a weight for local feature data not present at the similar depth position), from the storage unit 3. Here, the weight coefficients k11 and k12 satisfy k11>k12 and k11+k12=1.0.

Processes in Steps S18 and S19 are similar to those in Steps S8 and S9 in FIG. 2, respectively.

According to the second embodiment of the disclosure described above, since a weight is set for local feature data in each local area in an intraluminal image and the local feature data is integrated based on the weight, it is possible to calculate local feature data with which an object can be identified with high accuracy.

In addition, according to the second embodiment, since a weight is set in accordance with a characteristic of local feature data, the local feature data can be calculated with higher accuracy. In particular, by relatively increasing the weight for the mucosal area present at the depth position similar to the corresponding specific candidate area, higher accuracy of the local feature data can be realized.

In the second embodiment, the area characteristic calculator 521 may determine a type of an organ where the specific candidate area is present by using, for example, a method disclosed in JP 2008-278965 A. In that case, the weight setting unit 52 may determine a weight in accordance with the type of the organ. For example, regarding an organ to be examined, the weight setting unit 52 may set high extraction density for local feature data.

In the second embodiment, the area characteristic calculator 521 may determine a type of a specific candidate area. In that case, the weight setting unit 52 may determine a weight in accordance with the type of the specific candidate area. For example, the weight setting unit 52 may set high extraction density for specific candidate areas of erosion, an ulcer, an aphtha, a polyp, and the like, which are difficult to detect, while setting low extraction density for specific candidate areas of bleeding and the like, which are easy to detect. Determination standards may be determined based on pixel values of each of R, G, and B components in erosion, an ulcer, an aphtha, a polyp, bleeding, and the like collected in advance, or feature data secondarily calculated through known conversion based on the pixel values, and the type of the specific candidate area may be determined based on the determination standards.

Variation 2-1

Another example (second example) of an area characteristic calculation process performed by the area characteristic calculator 521 will be described.

First, the area characteristic calculator 521 extracts a same mucosal area by a method for dividing into closed areas which do not include a groove or a contour and to inside of which a groove or a contour does not enter, based on a known dynamic contour extraction method (for example, see JP 2012-45057 A and JP 2012-45055 A).

Then, the area characteristic calculator 521 determines whether the specific candidate area and the corresponding local areas are the same mucosal area.

In the case of the present variation 2-1, the weight setting unit 52 sets a large integration ratio for the local feature data present in the same mucosal area as the corresponding specific candidate area. Specifically, the weight setting unit 52 reads predetermined weight coefficients k21 (=a weight for local feature data present in the same mucosal area), and k22 (=a weight for local feature data not present in the same mucosal area), from the storage unit 3. Here, the weight coefficients k21 and k22 satisfy k21>k22 and k21+k22=1.0.

Variation 2-2

Another example (third example) of the area characteristic calculation process performed by the area characteristic calculator 521 will be described.

First, the area characteristic calculator 521 calculates color feature data (such as an average value of YCbCr, an average value of HSI, an average value of G/R) in local areas.

Then, the area characteristic calculator 521 extracts an area which exhibits intense red and white based on determination standards generated in advance, similarly to the specific candidate area extraction process by the specific candidate area extracting unit 21.

In that case, the weight setting unit 52 sets a large integration ratio for the local feature data present in the area which exhibits intense red or white. Specifically, the weight setting unit 52 reads predetermined weight coefficients k31 (=a weight for local feature data present in the area which exhibits intense red or white), and k32 (=a weight for local feature data not present in the area which exhibits intense red or white), from the storage unit 3. Here, the weight coefficients k31 and k32 satisfy k31>k32 and k31+k32=1.0.

Variation 2-3

Another example (fourth example) of the area characteristic calculation process performed by the area characteristic calculator 521 will be described.

First, the area characteristic calculator 521 calculates texture feature data (such as LBP, variance, kurtosis, and skewness) in local areas.

Then, the area characteristic calculator 521 extracts an area which exhibits a prominent change in irregularities on a mucosal surface based on determination standards generated in advance, similarly to the specific candidate area extraction process by the specific candidate area extracting unit 21.

In that case, the weight setting unit 52 sets a large integration ratio for the local feature data present in the area which exhibits the prominent change in irregularities on the mucosal surface. Specifically, the weight setting unit 52 reads predetermined weight coefficients k41 (=a weight for local feature data present in the area which exhibits the prominent change in irregularities on the mucosal surface), and k42 (=a weight for local feature data not present in the area which exhibits the prominent change in irregularities on the mucosal surface), from the storage unit 3. Here, the weight coefficients k41 and k42 satisfy k41>k42 and k41+k42=1.0.

It goes without saying that the above-described variations 2-1 to 2-3 have similar effects as the second embodiment.

Third Embodiment

Figure 13:
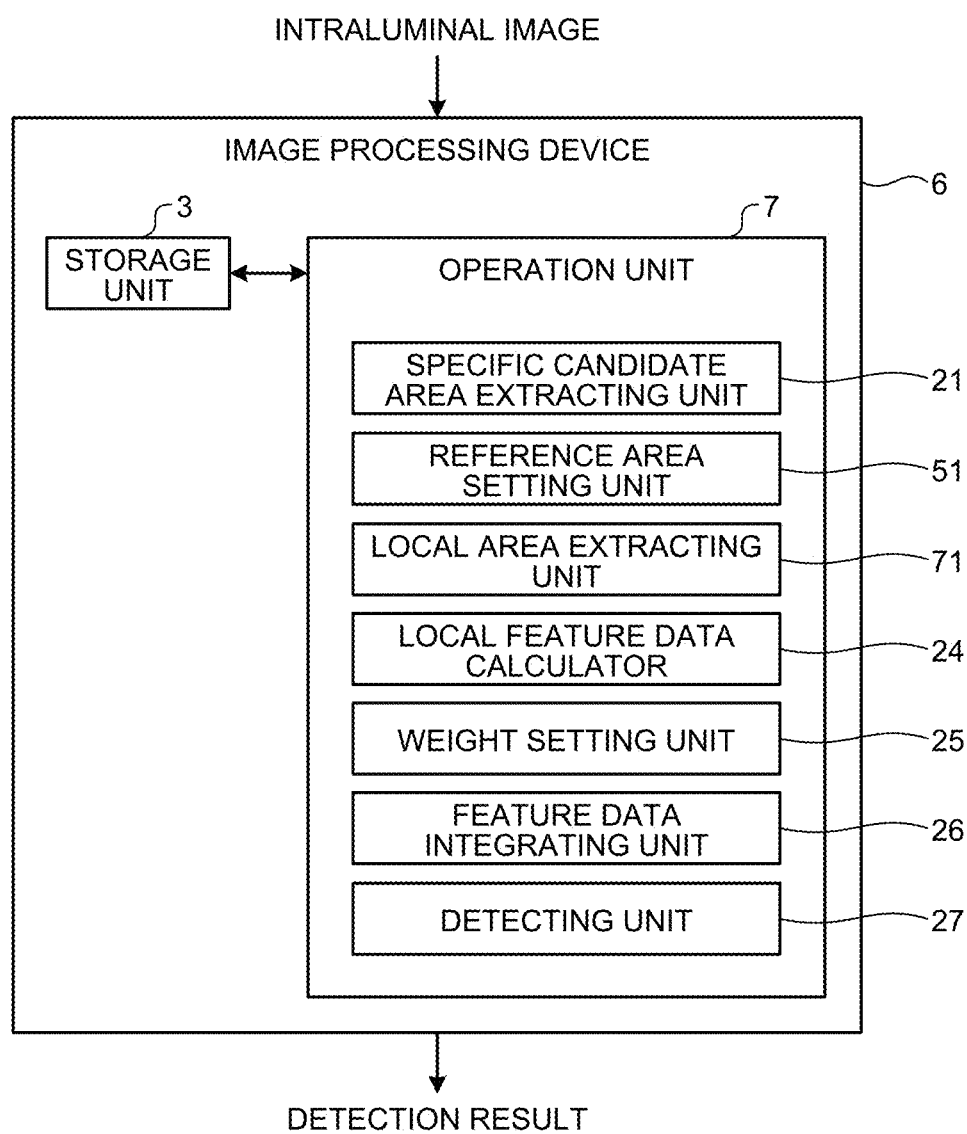
FIG. 13 is a block diagram illustrating a functional configuration of an image processing device according to a third embodiment of the disclosure.

FIG. 13 is a block diagram illustrating a functional configuration of an image processing device according to a third embodiment of the disclosure. The image processing device 6 illustrated in the figure includes an operation unit 7 and a storage unit 3. In the following description, the same reference signs are attached to components similar to those included in the operation unit 2 of the image processing device 1 according to the first embodiment.

The operation unit 7 includes a specific candidate area extracting unit 21, a reference area setting unit 51, a local area extracting unit 71, a local feature data calculator 24, a weight setting unit 25, a feature data integrating unit 26, and a detecting unit 27.

The local area extracting unit 71 calculates color information of a reference area, and extracts local areas based on the calculated color information.

Figure 14:
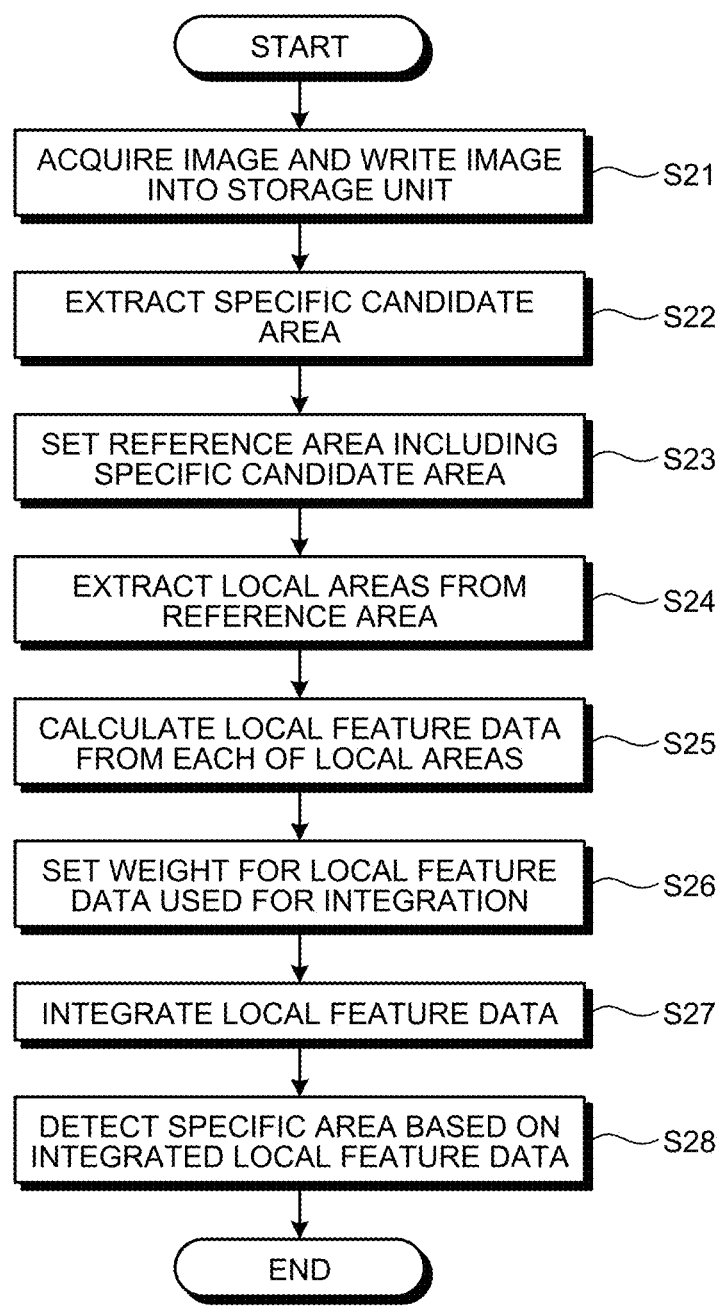
FIG. 14 is a flowchart illustrating an outline of a process performed by the image processing device according to the third embodiment of the disclosure.

FIG. 14 is a flowchart illustrating an outline of a process performed by the image processing device 6. Processes in Steps S21 to S23 are similar to those in Steps S1 to S3 in FIG. 2, respectively.

In Step S24, the local area extracting unit 71 extracts local areas from the reference area (Step S24). Hereinbelow, an outline of a local area extraction process performed by the local area extracting unit 71 will be described.

First, the local area extracting unit 71 calculates a luminance value of each pixel in the reference area.

Subsequently, the local feature data calculator 24 calculates gradient information of the luminance value by a filter such as Sobel, Laplacian, or the like.

Then, the local area extracting unit 71 divides the reference area into small areas based on the gradient information by a known watershed method or the like.

The local area extracting unit 71 calculates color feature data (such as an average value of RGB, an average value of YCbCr, an average value of HSI, an average value of G/R, and an average value of B/G) in the small areas.

Finally, the local area extracting unit 71 integrates, regarding the small areas, areas having similar color feature data, and extracts the integrated area as a local area. Although similar areas are integrated by the above-described known area integration method here, any method may be used as long as division into similar areas can be performed.

Steps S25 to S28 sequentially correspond to Steps S5 and S7 to S9 in FIG. 2. In the third embodiment, there is no need to perform division setting such that the reference area is divided into a border area and an internal area.

According to the third embodiment of the disclosure described above, since a weight is set for local feature data in each local area in an intraluminal image and the local feature data is integrated based on the weight, it is possible to calculate local feature data with which an object can be identified with high accuracy.

In addition, according to the third embodiment, since feature data in an image of a reference area is calculated and local areas are extracted based on the feature data, the local areas can be extracted with high accuracy. As a result, highly accurate local feature data can be obtained.

The local area extracting unit 71 may calculate texture feature data (such as LBP, variance, skewness, and kurtosis) in the small areas instead of calculating color feature data in the small areas, and extract local areas based on the calculated texture information. In that case, the local area extracting unit 71 integrates areas having similar texture feature data, and extracts the integrated area as a local area.

Other Embodiments

Hereinabove, the modes for carrying out the present invention have been described. However, the present invention should not be limited exclusively to the first to third embodiments described above. For example, although the reference area setting unit 22 sets the reference area by expanding the specific candidate area in accordance with the above expression (1) in the first embodiment, the reference area may be set by reducing the specific candidate area.

In addition, it is possible to generate learning data by using the local feature data integrated by the feature data integrating unit 26.

As describe above, the disclosure can include various embodiments which are not described herein.

According to some embodiments, since a weight depending on each of local areas in an intraluminal image is set to integrate local feature data of the local areas, it is possible to calculate local feature data with which an object can be identified with high accuracy.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing device comprising:
    a processor comprising hardware, wherein the processor is configured to:
        extract a specific candidate area that satisfies a predetermined condition from an intraluminal image captured inside a body lumen;
        set a reference area that includes at least a part of the specific candidate area extracted;
        extract local areas based on the reference area set;
        calculate local feature data that is feature data of each of the local areas extracted;
        set a weight depending on each of the local areas extracted based on the specific candidate area extracted; and
        integrate the local feature data.

2. The image processing device according to claim 1, wherein the processor is configured to:
    set a weight for the local feature data; and
    integrate the local feature data based on the weight for the local feature data.

3. The image processing device according to claim 1, wherein the processor is configured to:
    set, as a weight, extraction density used when the processor extracts each of the local area; and
    extract the local areas extracted in accordance with the extraction density set.

4. The image processing device according to claim 1, wherein the processor is configured to perform division setting such that the reference area set is divided into at least a border area and an internal area.

5. The image processing device according to claim 4, wherein the processor is configured to set a higher weight for the border area than for the internal area.

6. The image processing device according to claim 1, wherein the processor is configured to:
    calculate a characteristic of each of the local areas; and
    set a weight in accordance with the characteristic of each of the local areas.

7. The image processing device according to claim 6, wherein the processor is configured to extract a mucosal area present at a depth position similar to the specific candidate area extracted.

8. The image processing device according to claim 6, wherein the processor is configured to extract a same mucosal area as the specific candidate area extracted.

9. The image processing device according to claim 6, wherein the processor is configured to calculate, as the characteristic, at least one of a color characteristic and a texture characteristic of each of the local areas extracted.

10. The image processing device according to claim 6, wherein the processor is configured to:
    determine a type of an organ where the specific candidate area extracted is present; and
    set a weight in accordance with the type of the organ.

11. The image processing device according to claim 6, wherein the processor is configured to:
    determine a type of the specific candidate area extracted; and
    set a weight in accordance with the type of the specific candidate area extracted.

12. The image processing device according to claim 1, wherein the processor is configured to:
    calculate feature data in an image of the reference area set; and
    extract the local areas extracted based on the feature data in the image of the reference area set.

13. The image processing device according to claim 12, wherein the feature data is color information.

14. The image processing device according to claim 12, wherein the feature data is texture information.

15. The image processing device according to claim 1, wherein the processor is configured to detect the specific candidate area extracted based on the local feature data integrated.

16. An image processing method comprising:
    extracting a specific candidate area that satisfies a predetermined condition from an intraluminal image captured inside a body lumen;
    setting a reference area that includes at least a part of the specific candidate area extracted;
    extracting local areas based on the reference area set;
    calculating local feature data that is feature data of each of the local areas extracted;
    setting a weight depending on each of the local areas extracted based on the specific candidate area extracted; and
    integrating the local feature data.

17. A non-transitory computer-readable recording medium recording an image processing program for causing a computer to execute:
    extracting a specific candidate area that satisfies a predetermined condition from an intraluminal image captured inside a body lumen;
    setting a reference area that includes at least a part of the specific candidate area extracted;
    extracting local areas based on the reference area set;
    calculating local feature data that is feature data of each of the local areas extracted;
    setting a weight depending on each of the local areas extracted based on the specific candidate area extracted; and
    integrating the local feature data.

* * * * *